(12) United States Patent
Filion et al.

(10) Patent No.: US 10,165,743 B2
(45) Date of Patent: Jan. 1, 2019

(54) RHIZOBACTERIAL STRAIN AND USES FOR ENHANCING TOTAL LIPID YIELDS IN AN OILSEED CROP

(71) Applicants: Martin Filion, Moncton (CA); Marc Surette, Moncton (CA)

(72) Inventors: Martin Filion, Moncton (CA); Marc Surette, Moncton (CA)

( * ) Notice: Subject to any disclaimer, the term of this patent is extended or adjusted under 35 U.S.C. 154(b) by 0 days.

(21) Appl. No.: 15/471,135

(22) Filed: Mar. 28, 2017

(65) Prior Publication Data

US 2018/0279570 A1     Oct. 4, 2018

(51) Int. Cl.
| | | |
|---|---|---|
| *A01H 3/00* | (2006.01) |
| *A01H 5/10* | (2018.01) |
| *A01N 63/00* | (2006.01) |

(52) U.S. Cl.
CPC .............. *A01H 3/00* (2013.01); *A01H 5/10* (2013.01); *A01N 63/00* (2013.01)

(58) Field of Classification Search
None
See application file for complete search history.

(56) References Cited

U.S. PATENT DOCUMENTS

| | | |
|---|---|---|
| 5,503,651 A | 4/1996 | Kloepper et al. |
| 8,796,179 B2 | 8/2014 | Levenfors et al. |
| 9,101,144 B2 | 8/2015 | Doktycz et al. |
| 9,295,263 B2 | 3/2016 | von Maltzahn et al. |
| 9,408,394 B2 | 8/2016 | von Maltzahn et al. |

FOREIGN PATENT DOCUMENTS

| | | |
|---|---|---|
| CA | 2841043 C | 2/2015 |
| WO | WO2014079814 A1 | 5/2014 |
| WO | WO2015181009 A1 | 12/2015 |
| WO | WO2015183003 A1 | 12/2015 |

OTHER PUBLICATIONS

Shehata et al 2012 (Australian Journal of Basic and Applied Sciences 6:4 p. 98-107).*
Abbadi et al 2004 (The Plant Cell 16: p. 2734-2748).*
Gadkar and Filion 2015 (SpringerPlus 4: p. 1-12).*

* cited by examiner

*Primary Examiner* — Matthew R Keogh
(74) *Attorney, Agent, or Firm* — Benoit & Cote Inc.; France Cote

(57) ABSTRACT

There is described an isolated rhizobacterial strain for enhancing total lipid yields in an oilseed crop having a nucleic acid molecule comprising a nucleotide sequence consisting of SEQ ID NO.:1; or the nucleotide sequence SEQ ID NO.:1 having a substitution, a deletion and/or an addition of one or more nucleotide; or a nucleotide sequence having sufficient homology with the nucleotide sequence SEQ ID NO.:1 for enhancing total lipid yields, or a nucleotide sequence capable of hybridization with a first primer consisting of SEQ ID NO.:2; and/or a second primer consisting of SEQ ID NO.:3; and/or a nucleotide sequence capable of hybridization with a probe consisting of SEQ ID NO.:4; and variants thereof.

4 Claims, 4 Drawing Sheets

Specification includes a Sequence Listing.

SEQUENCE LISTING

```
<160> NUMBER OF SEQ ID NOS: 5

<210> SEQ ID NO 1
<211> LENGTH: 62
<212> TYPE: DNA
<213> ORGANISM: Pseudomonas fluorescens

<400> SEQUENCE: 1
gcctgcatcg cggtcttgat catagactcg gaattgtccg cgccaatgat cacccgattg      60
gg                                                                    62

<210> SEQ ID NO 2
<211> LENGTH: 17
<212> TYPE: DNA
<213> ORGANISM: Pseudomonas fluorescens

<400> SEQUENCE: 2
gcctgcatcg cggtctt                                                    17

<210> SEQ ID NO 3
<211> LENGTH: 19
<212> TYPE: DNA
<213> ORGANISM: Pseudomonas fluorescens

<400> SEQUENCE: 3
cccaatcggg tgatcattg                                                  19

<210> SEQ ID NO 4
<211> LENGTH: 19
<212> TYPE: DNA
<213> ORGANISM: Pseudomonas fluorescens

<400> SEQUENCE: 4
atcatagact cggaattgt                                                  19

<210> SEQ ID NO 5
<211> LENGTH: 216
<212> TYPE: DNA
<213> ORGANISM: Pseudomonas fluorescens

<400> SEQUENCE: 5
ctacggcaag gcgacgctga cgtgtgcaaa ggttgtaccc gtttcaccac atcagccggc      60
tgcgcctgca tcgcggtctt gatcatagac tcggaattgt ccgcgccaat gatcacccga     120
ttgggttttt ccgccagcaa cggccagaaa cgccctgcac cacacggcag atccagaacc     180
agccccggct cgccgtcag cgtcgccttg ccgtag                                216
```

RHIZOBACTERIAL STRAIN AND USES FOR ENHANCING TOTAL LIPID YIELDS IN AN OILSEED CROP

BACKGROUND

(a) Field

The subject matter disclosed generally relates to a rhizobacterial strain and uses for enhancing total lipid yields in an oilseed crop. More particularly, the strain is *Pseudomonas fluorescens* (LBUM677).

(b) Related Prior Art

The narrow region of soil that is directly influenced by root secretions and associated soil microorganisms is called the "rhizosphere". The rhizosphere can have an influence on plant growth, the number of seeds produced per plant, seed weight and/or seed oil content via the action of various strains of bacteria in different crops, including cereals and oilseeds crops (de Freitas, J. R., et al., *Soil Biology and Biochemistry*, 1992. 24(11): p. 1137-1146; Kloepper, J. W., et al. *Plant Disease*, 1988. 72(1): p. 42-46; U.S. Pat. No. 5,503,651).

Plant growth promoting rhizobacteria (PGPR) defined the microorganisms inhabiting the rhizosphere of plants. Among this taxonomically diverse group, *Pseudomonas* spp. and *Bacillus* spp. are common soil inhabitants. More precisely, strains of *Pseudomonas* spp. are predominantly found in the rhizosphere, in part due to their capacity at using various nutrients released through root exudation. The compatibility existing between a given *Pseudomonas* spp. strain and a given plant species needs to be tested for a plant to acquire the growth beneficial effects associated with *Pseudomonas* spp. colonization. In fact, no microbial inoculum can be considered universal as numerous biotic and abiotic factors, such as the plant's genotype, soil characteristics, crop rotation, irrigation and application of agrichemicals, just to name a few, strongly impact on rhizocompetence and plant growth promotion capabilities.

As such, little is known regarding the impact of *Pseudomonas* spp. colonization at promoting oilseed crops' growth and seed lipid accumulation. Among oilseed crops of commercial interest, *Glycine max* and *Brassica napus* are rich sources of oleic, linoleic and α-linolenic acids. In fact, the consumption of these fatty acids has been shown to positively impact human health via blood pressure lowering, improvement of glucose control and insulin sensitivity, reduction of blood cholesterol and triacylglycerol concentrations, and inflammation (Lee, J. H., et al. *Nature Reviews Cardiology*, 2009. 6(12): p. 753-758).

One of these beneficial fatty acids is a plant-derived omega-3 polyunsaturated fatty acid called Stearidonic acid (SDA; 18:4 n-3). More precisely, it has been shown that dietary SDA is efficiently metabolized into eicosapentaenoic acid (EPA; 20:5 n-3; FIG. 1) and provides human health benefits similar to those associated with the consumption of marine oils, containing high levels of EPA and docosahexaenoic acid (DHA; 22:6 n-3). However, marine oil alternatives are currently being investigated due to public concern regarding their contamination with heavy metals and toxins, and the uncertainty of future available stocks due to overfishing (Kris-Etherton, P. M., et al. *Circulation*, 2002. 106 (21): p. 2747-2757). For these reasons, SDA could become a viable substitute for marine-derived EPA and DHA, thus showing its potential as an additive in fortified food products.

Although SDA is not a common fatty acid found in the plant kingdom, the Boraginaceae family contains several plant species known for producing amounts of SDA in their seeds, including corn gromwell (*Buglossoides arvensis*). However, the yield of total lipids and/or SDA is often low.

Therefore, it would be highly desirable to have a rhizobacterial strain capable of enhancing total lipid yields in an oilseed crop.

SUMMARY

According to a first embodiment, there is provided an isolated rhizobacterial strain for enhancing total lipid yields in an oilseed crop having a nucleic acid molecule comprising a nucleotide sequence consisting of:

```
                                          (SEQ ID NO.: 1)
5'GCCTGCATCGCGGTCTTGATCATAGACTCGGAATTGTCCGCGCCAAT
GATCACCCGATTGGG3'
``` or the nucleotide sequence SEQ ID NO.:1 having a substitution, a deletion and/or an addition of one or more nucleotide, or a nucleotide sequence having a sufficient homology with the nucleotide sequence SEQ ID NO.:1 for enhancing total lipid yields in the oilseed crop, or a nucleotide sequence capable of hybridization with a first primer consisting of:

```
                                          (SEQ ID NO.: 2)
                         5'GCCTGCATCGCGGTCTT3'
``` and/or a second primer consisting of:

```
                                          (SEQ ID NO.: 3)
                         5'CCCAATCGGGTGATCATTG3'
``` and/or a nucleotide sequence capable of hybridization with a probe consisting of:

```
                                          (SEQ ID NO.: 4)
                         5'ATCATAGACTCGGAATTGT3'.
```

The nucleotide sequence of SEQ ID NO.: 1 is located within the following nucleotide sequence consisting of: 5'CTACGGCAAGGCGACGCTGACGTGTGCAAAGGT-TGTACCCGTTTCACCAC ATCAGCCGGCTGCGCCTG-CATCGCGGTCTTGATCATAGACTCGGAATTGTC CGCGCCAATGATCACCCGATTGGGTTTTTCCGCCA-GCAACGGCCAGAAACG CCCTGCACCACACGGCA-GATCCAGAACCAGCCCCGGCTCGCCCGTCAGCG TCGCCTTGCCGTAG3' (SEQ ID NO.:5) which is specific to the present rhizobacterial strain.

The isolated rhizobacterial strain is preferably having a nucleotide sequence of at least about 80% homology with the nucleotide sequence SEQ ID NO.:1.

The isolated rhizobacterial strain is preferably *Pseudomonas fluorescens* (LBUM677).

The most preferred isolated *Pseudomonas fluorescens* strain for enhancing total lipid yields in an oilseed crop is deposited under ATCC Patent Deposit Designation No. PTA-123874 on Mar. 9, 2017.

According to a second embodiment, there is provided a bacterial culture comprising essentially at least one strain of the present invention in association with a biologically acceptable carrier, wherein the strain retains a capacity for enhancing total lipid yields in the oilseed crop.

The preferred oilseed crop may be selected from the group consisting of soy (*Glycine max*), canola (*Brassica napus*) and corn gromwell (Buglossoides *arvensis*).

When inoculating an oilseed crop with the bacterial culture of the present invention, the rhizobacterial strain enhances growth yields of the oilseed crop by at least 15% to 215% relative to oilseed crop not exposed to the rhizobacterial strain.

When inoculating an oilseed crop with the bacterial culture of the present invention, the rhizobacterial strain enhances seed yields of the oilseed crop by at least 10% to 45% relative to oilseed crop not exposed to the rhizobacterial strain.

When inoculating an oilseed crop with the bacterial culture of the present invention, the rhizobacterial strain enhances total lipid yields of the oilseed crop by at least 10% to 45% relative to oilseed crop not exposed to the rhizobacterial strain.

When inoculating an oilseed crop with the bacterial culture of the present invention, the rhizobacterial strain enhances total lipid yields including stearidonic acid in the *Buglossoides arvensis* crop by at least 10% to 45% relative to *Buglossoides arvensis* crop not exposed to the rhizobacterial strain.

According to a third embodiment, there is provided use of isolated rhizobacterial strain or bacterial culture of the present invention for inoculating the oilseed crop for enhancing total lipid yields.

According to a fourth embodiment, there is provided a method for enhancing the oilseed crop total lipid yields comprising a step of inoculating the oilseed crop with an isolated rhizobacterial strain or with a bacterial culture of the present invention, at a quantity of at least $1 \times 10^7$ to $1 \times 10^9$ bacterial cells/plant.

The method preferably includes a further step of extracting seed oil at seed maturity.

According to a fifth embodiment, there is provided an inoculated oilseed crop obtained by inoculating the oilseed crop with a bacterial culture of the present invention for enhancing total lipid yields.

The following terms are defined below.

The term "enhancing yield" is intended to mean any improvement in the yield of the plant and/or any measured plant product, such as seed. In accordance with the invention, changes in different phenotypic traits may improve yield. For example, and without limitation, parameters such as plant weight, seed number, seed weight, total lipids and stearidonic acid, are suitable measurements of an improved yield.

The term "homology" is intended to mean the number of positions in the two optimally aligned nucleotide sequences which have identical residues divided by the number of positions, expressed as a percentage. A gap, i.e., a position in an alignment where a residue is present in one sequence but not in the other is regarded as a position with non-identical residues. The alignment of the two sequences is performed by BLAST (NCBI).

The term "inoculating" or "inoculation" is intended to mean a process to deliver any form of a rhizobacterial strain, which are capable of propagating on or in a substrate (e.g., a soil, a plant or plant part, etc.) when the conditions of temperature, moisture, etc., are favorable for microbial growth.

The term "biologically acceptable carrier" is intended to mean an any material which can be used to deliver the actives (e.g., rhizobacterial strain) to a plant or plant part (e.g., plant roots, etc.), and preferably which carrier can be applied to a plant or plant part with minimal adverse effect or without having an adverse effect on other non-target plants, soil structure or soil drainage.

Features and advantages of the subject matter hereof will become more apparent in light of the following detailed description of selected embodiments, as illustrated in the accompanying Figs. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
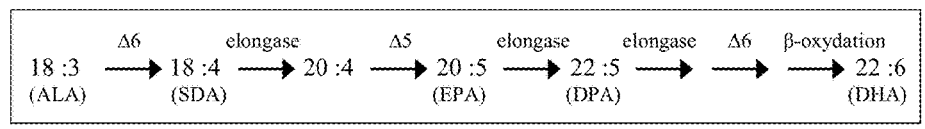
FIG. 1 illustrates the omega-3 polyunsaturated fatty acid metabolism pathway in human.

A preliminary screening experiment is performed in order to assess total seed number, total lipid yield and SDA yield of the *B. arvensis* plants inoculated with the 40 rhizobacterial isolates gave varying results when their levels were compared to those of the control plants (Table 1). Five rhizobacterial isolates increased the total lipid yield and the SDA yield by at least 20%: LBUM288, LBUM361, LBUM395, LBUM570 and LBUM677. These isolates are subsequently used in a second growth chamber screening experiment.

TABLE 1

16S rDNA identification and preliminary results of the 40 rhizobacteria isolates screened for their ability to enhance *B. arvensis* SDA yield in pots experiments.

| Strains | 16S Identification BLAST Results | Homology | Accession # | Preliminary results (% vs respective control) Seed number | Seed weight | SDA yield | Lipid yield | Seed yield |
|---|---|---|---|---|---|---|---|---|
| LBUM149 | *Arthrobacter* sp. strain S21004 | 1477/1479 (99%) | D84562.2 | 15.5 | −9.9 | −0.7 | 7.0 | 3.5 |
| LBUM270 | *Arthrobacter ramosus* strain DSM 20546 | 1403/1410 (99%) | NR_026193.1 | 13.2 | −3.2 | 17.7 | 11.3 | 10.1 |
| LBUM476 | *Bacillus cereus* strain TA2 | 1474/1475 (99%) | GQ381280.1 | 0.9 | −3.7 | −1.1 | 2.1 | −3.1 |
| LBUM676 | *Bacillus cereus* strain TA2 | 1489/1491 (99%) | GQ381280.1 | 9.3 | 2.0 | 14.4 | 15.4 | 10.5 |
| LBUM629 | *Bacillus cereus* strain 13635K | 1494/1498 (99%) | EU741083.1 | −14.3 | 0.3 | −15.8 | −4.2 | −15.4 |
| LBUM375 | *Bacillus fusiformis* strain SW-B9 | 1449/1468 (98%) | AY907676.1 | 1.3 | 0.2 | −2.3 | 5.7 | 1.6 |
| LBUM120 | *Bacillus globisporus* | 1469/1493 (98%) | X68415.1 | 1.0 | −6.2 | −6.4 | −5.3 | −5.1 |
| LBUM211 | *Bacillus megaterium* strain HJ024 | 1431/1432 (99%) | GQ152133.1 | 3.4 | 20.9 | 7.8 | 3.5 | 21.0 |
| LBUM407 | *Bacillus megaterium* strain TSIW36 | 1499/1505 (99%) | FM164631.1 | 4.7 | 13.1 | 17.6 | 2.0 | 17.3 |
| LBUM139 | *Bacillus pumilus* strain SAFR-032 | 1491/1493 (99%) | CP000813.1 | −7.2 | 0.6 | 6.3 | 0.0 | −5.5 |
| LBUM190 | *Bacillus simplex* strain N25 | 1492/1498 (99%) | GU086427.1 | 2.3 | 16.7 | 8.3 | 16.8 | 14.8 |
| LBUM288 * | *Bacillus subtilis* strain C8-4 | 1491/1492 (99%) | EU257436.1 | 18.4 | 1.7 | 30.5 | 26.8 | 20.3 |
| LBUM203 | *Bacillus weihenstephanensis* strain AB11A | 1493/1495 (99%) | AM062676.1 | −5.6 | 16.4 | 8.4 | 6.6 | 6.7 |
| LBUM112 | *Paenibacillus polymyxa* strain DC-4 | 801/803 (99%) | GQ375783.1 | −13.0 | 25.0 | 4.4 | 2.2 | 5.8 |
| LBUM176 | *Paenibacillus polymyxa* strain ISSDS-851 | 1483/1494 (99%) | EF634024.1 | 7.0 | −0.2 | 15.0 | 11.8 | 5.5 |
| LBUM298 | *Paenibacillus polymyxa* strain ISSDS-851 | 1482/1493 (99%) | EF634024.1 | 15.5 | −18.2 | −6.5 | −3.1 | −5.2 |
| LBUM151 | *Flavobacterium* sp. strain WB4.4-89 | 1454/1467 (99%) | AM934675.1 | 20.0 | −16.3 | −0.3 | −3.6 | −0.5 |
| LBUM345 | *Klebsiella* sp. | 1475/1480 (99%) | DQ279306.1 | 6.7 | −1.1 | 9.6 | 12.0 | 6.1 |
| LBUM628 | *Phyllobacterium* sp. | 1426/1427 (99%) | AJ968699.1 | 4.8 | 3.1 | 22.0 | 12.8 | 8.4 |
| LBUM643 | *Phyllobacterium* sp. strain T1018 | 1426/1427 (99%) | AJ968699.1 | 6.3 | 7.5 | 22.1 | 25.3 | 14.9 |
| LBUM570 * | *Pseudomonas* sp. strain BIM B-86 | 1450/1451 (99%) | GU784939.1 | 15.5 | 6.5 | 26.2 | 23.1 | 22.7 |
| LBUM395 * | *Pseudomonas* sp. strain CA-1 | 1480/1482 (99%) | DQ984202.1 | 10.1 | 20.6 | 26.2 | 26.4 | 29.6 |
| LBUM239 | *Pseudomonas brassicacearum* strain 520-1 | 1471/1477 (99%) | AJ292381.1 | −15.4 | 12.6 | −12.0 | −5.8 | 5.8 |
| LBUM300 | *Pseudomonas brassicacearum* strain 520-1 | 1474/1476 (99%) | AJ292381.1 | −1.4 | 1.3 | −4.0 | −3.9 | −0.9 |
| LBUM636 | *Pseudomonas collierea* strain PR212T | 1465/1466 (99%) | AM421016.2 | 5.3 | 6.3 | 9.6 | −1.7 | 11.3 |
| LBUM647 | *Pseudomonas corrugate* | 1473/1481 (99%) | AF348508.1 | 1.4 | 11.1 | 7.6 | 4.5 | 12.8 |
| LBUM770 | *Pseudomonas fluorescens* strain Pf29A | 1472/1476 (99%) | DQ473439.1 | 1.2 | 2.6 | −5.2 | −5.0 | 2.4 |
| LBUM825 | *Pseudomonas fluorescens* strain Pf-5 | 1480/1482 (99%) | CP000076.1 | −2.1 | 17.7 | 13.5 | 14.5 | 13.2 |
| LBUM229 | *Pseudomonas fluorescens* strain TM5-2 | 1461/1461 (100%) | AB204715.1 | 5.2 | 5.4 | 13.7 | 11.9 | 10.8 |

TABLE 1-continued 16S rDNA identification and preliminary results of the 40 rhizobacteria isolates screened for their ability to enhance *B. arvensis* SDA yield in pots experiments.

| | | | | Preliminary results (% vs respective control) | | | | |
|---|---|---|---|---|---|---|---|---|
| Strains | 16S Identification BLAST Results | Homology | Accession # | Seed number | Seed weight | SDA yield | Lipid yield | Seed yield |
| LBUM677 * | *Pseudomonas fluorescens* strain strain 9zhy | 1475/1479 (99%) | AM410631.1 | 22.4 | 1.8 | 39.6 | 33.8 | 25.0 |
| LBUM364 | *Pseudomonas graminis* strain KF701 | 1406/1409 (99%) | AB109886.1 | 1.1 | 20.0 | −6.0 | 13.6 | 18.0 |
| LBUM223 | *Pseudomonas libanensis* strain CIP | 1444/1447 (99%) | NR_024901.1 | −18.9 | 2.5 | −31.5 | −23.8 | −16.8 |
| LBUM309 | *Pseudomonas mandelii* strain Asd MV-11 | 766/771 (99%) | FM955880.1 | −1.9 | −10.0 | −4.3 | −8.9 | −11.3 |
| LBUM285 | *Pseudomonas putida* strain PC36 | 1470/1473 (99%) | DQ178233.1 | 1.3 | 0.3 | 7.3 | 1.6 | 1.9 |
| LBUM437 | *Pseudomonas putida* strain Tg | 1471/1478 (99%) | EU275363.1 | 14.3 | −5.8 | 14.4 | 6.5 | 7.9 |
| LBUM609 | *Pseudomonas putida* strain Tg | 1484/1490 (99%) | EU275363.1 | 13.0 | −6.6 | 13.3 | 15.4 | 5.6 |
| LBUM376 | *Pseudomonas reinekei* strain MT1T | 1464/1470 (99%) | AM293565.1 | 11.4 | 8.1 | 18.0 | 27.0 | 17.2 |
| LBUM228 | *Stenotrophomonas rhizophila* strain Gd2T | 1490/1492 (99%) | GU391467.1 | −0.2 | −11.5 | −2.2 | −13.0 | −13.0 |
| LBUM340 | *Stenotrophomonas rhizophila* strain Asd M1-7 | 1484/1487 (99%) | FM955853.1 | 18.9 | −8.5 | 14.8 | 9.9 | 9.5 |
| LBUM361 * | *Stenotrophomonas rhizophila* strain Asd M1-7 | 1425/1431 (99%) | FM955853.1 | 26.3 | −0.2 | 23.0 | 25.3 | 23.8 |

During the second plant screening experiment, shoot fresh weight is significantly affected by PGPR treatment (Table 2). However, this increase diminished over time. At 4 weeks, four of the rhizobacterial inoculated treatments had significantly higher shoot weights (ranging from 21% to 35% above controls; $P<0.05$), and this diminished to three inoculated treatments at 8 weeks (from 12 to 24% above controls; $P<0.05$) and when the shoot weight of rhizobacterial inoculated treatments were compared with the non-inoculated controls at 12 weeks, no significant differences were observed. A significant increase in the total seed number was observed for three of the PGPR inoculated treatments (Table 3). A 16% increase (as compared to control) was observed with the strains LBUM288 ($P=0.02$) and LBUM361 ($P=0.02$), while LBUM570 showed a 15% increase ($P=0.03$). The total seed weight per plant was significantly higher for all treatments as compared to the control ($P<0.001$; Table 4).

TABLE 2

Effect of selected PGPR on *B. arvensis* shoot height and fresh weight at 4, 8 and 12 weeks following inoculation.

| | | 4 Weeks | | 8 Weeks | | 12 Weeks | |
|---|---|---|---|---|---|---|---|
| | Bacterial identification | Shoot Height (cm) | Shoot weight (g) | Shoot Height (cm) | Shoot weight (g) | Shoot Height (cm) | Shoot weight (g) |
| Growth Chamber[a] | | | | | | | |
| Control | | 9.7 ± 0.46 | 2.98 ± 0.47 | 49.0 ± 1.38 | 8.07 ± 0.59 | 62.1 ± 3.19 | 8.21 ± 0.32 |
| LBUM288 | *Bacillus amyloliquefaciens* | 10.2 ± 0.48 | 4.00 ± 0.47* | 44.0 ± 1.45 | 10.02 ± 0.60* | 57.7 ± 3.21 | 8.62 ± 0.33 |
| LBUM361 | *Stenotrophomonas rhizophila* | 10 ± 0.46 | 3.18 ± 0.46 | 49.9 ± 1.38 | 8.60 ± 0.59 | 61.4 ± 3.23 | 8.29 ± 0.33 |
| LBUM395 | *Pseudomonas putida* | 10.1 ± 0.50 | 4.01 ± 0.47* | 44.3 ± 1.53 | 9.06 ± 0.60* | 55.8 ± 3.23 | 8.04 ± 0.33 |
| LBUM570 | *Pseudomonas fluorescens* | 9.4 ± 0.48 | 4.00 ± 0.47* | 49.4 ± 1.45 | 9.49 ± 0.60* | 59.2 ± 3.21 | 8.43 ± 0.33 |
| LBUM677 | *Pseudomona fluorescens* | 10.7 ± 0.46 | 3.59 ± 0.46* | 50.5 ± 1.32 | 8.32 ± 0.58 | 59.2 ± 3.21 | 7.92 ± 0.33 |

TABLE 2-continued

Effect of selected PGPR on *B. arvensis* shoot height and fresh weight at 4, 8 and 12 weeks following inoculation.

| | Bacterial identification | 4 Weeks | | 8 Weeks | | 12 Weeks | |
|---|---|---|---|---|---|---|---|
| | | Shoot Height (cm) | Shoot weight (g) | Shoot Height (cm) | Shoot weight (g) | Shoot Height (cm) | Shoot weight (g) |
| Field[b] | | | | | | | |
| Control | | 46.0 ± 0.7 | 27.86 ± 2.48 | 77.2 ± 1.6 | 26.98 ± 2.73 | —[c] | — |
| LBUM288 | *B. amyloliquefaciens* | 44.9 ± 1.3 | 25.40 ± 2.22 | 82.0 ± 1.8 | 32.46 ± 2.86 | — | — |
| LBUM361 | *S. rhizophila* | 44.4 ± 1.0 | 27.38 ± 2.70 | 81.6 ± 2.6 | 32.39 ± 6.73 | — | — |
| LBUM395 | *P. putida* | 45.7 ± 0.8 | 23.20 ± 2.07 | 78.8 ± 2.6 | 26.93 ± 2.56 | — | — |
| LBUM570 | *P. fluorescens* | 46.5 ± 1.0 | 30.86 ± 3.46 | 85.4 ± 2.3* | 35.14 ± 4.60 | — | — |
| LBUM677 | *P. fluorescens* | 47.4 ± 0.8 | 21.28 ± 2.61 | 80.9 ± 1.7 | 32.74 ± 3.52 | — | — |

TABLE 3

Effect of selected PGPR on seed productivity in *B. arvensis*.

| Treatment | Bacterial identification | Total seed number | Total seed weight (g)/plant | Total lipid yield (mg)/plant | SDA yield (mg)/plant | % SDA |
|---|---|---|---|---|---|---|
| Growth Chamber[a] | | | | | | |
| Control | | 215 ± 10 | 1.34 ± 0.08 | 322.0 ± 18.6 | 55.4 ± 4.5 | 18.0 ± 0.2 |
| LBUM288 | *Bacillus amyloliquefaciens* | 249 ± 10* | 1.62 ± 0.08* | 403.0 ± 18.9* | 71.0 ± 4.5* | 17.9 ± 0.2 |
| LBUM361 | *Stenotrophomonas rhizophila* | 250 ± 11* | 1.55 ± 0.08* | 386.0 ± 19.2* | 66.9 ± 4.6* | 18.0 ± 0.3 |
| LBUM395 | *Pseudomonas putida* | 233 ± 11 | 1.53 ± 0.08* | 373.0 ± 19.2* | 65.8 ± 4.6* | 17.9 ± 0.3 |
| LBUM570 | *Pseudomonas fluorescens* | 248 ± 11* | 1.63 ± 0.08* | 394.0 ± 18.9* | 69.0 ± 4.5* | 18.0 ± 0.2 |
| LBUM677 | *Pseudomonas fluorescens* | 240 ± 11 | 1.58 ± 0.08* | 367.0 ± 18.9* | 66.2 ± 4.5* | 18.1 ± 0.2 |
| Field[b] | | | | | | |
| Control | | 313 ± 29 | 2.12 ± 0.19 | 401.6 ± 37.1 | 80.8 ± 7.9 | 19.3 ± 0.3 |
| LBUM288 | *B. amyloliquefaciens* | 366 ± 34 | 2.19 ± 0.20 | 407.3 ± 36.4 | 77.2 ± 6.5 | 19.5 ± 0.2 |
| LBUM361 | *S. rhizophila* | 351 ± 57 | 2.05 ± 0.26 | 355.3 ± 36.3 | 69.7 ± 7.4 | 19.2 ± 0.2 |
| LBUM395 | *P. putida* | 305 ± 30 | 1.91 ± 0.19 | 343.4 ± 38.1 | 67.6 ± 7.3 | 19.1 ± 0.5 |
| LBUM570 | *P. fluorescens* | 376 ± 45 | 2.30 ± 0.29 | 465.0 ± 60.0 | 85.1 ± 11.0 | 19.4 ± 0.1 |
| LBUM677 | *P. fluorescens* | 381 ± 37 | 2.45 ± 0.22 | 497.6 ± 46.3 | 108.0 ± 10.8* | 19.5 ± 0.2 |

TABLE 4

| Plant species | Treatment | Palmitic C16:00 | Oleic C18:1n | Linoleic C18:2n-6 | α-Linolenic C18:3n-3 | SDA C18:4n-3 |
|---|---|---|---|---|---|---|
| *Glycine max* | LBUM | 126.10[a] | 172.38[a] | 619.62[a] | 106.76[a] | — |
| | Control | 95.59[b] | 133.57[b] | 480.86[b] | 85.45[b] | — |
| *Buglossoides arvensis* | LBUM | — | — | — | 219.24[a] | 527.82[a] |
| | Control | — | — | — | 182.35[b] | 423.20[b] |
| *Brassica napus* | LBUM | — | 895.18[a] | 301.72[a] | 153.84[a] | — |
| | Control | — | 618.17[b] | 227.43[b] | 108.80[b] | — |

Response of [a]*B. napus*', [b]*B. arvensis*' and c) *G. max*' total oil yield per plant to *P. fluorescens* LBUM677 inoculation.

All PGPR inoculations resulted in significantly increased lipid yields and SDA yields as compared to the controls at 12 weeks following bacterial inoculations (Table 3). The lipid yields were increased from 14% to 25% with PGPR inoculations (P<0.05 for all treatments); while the SDA yields were increased from 18% to 24% in all treatments (P<0.001 for all). Seeds harvested from control plants had an average oil content of 240.6 µg oil/mg seed and an SDA content of 41.4 µg SDA/mg seed. The highest increase in lipid yield and total SDA yield was noted with LBUM288 (25% and 28% above control), while the smallest increases were observed with LBUM677 for the lipid yield (14%) and LBUM395 for the total SDA yield (19%). SDA consisted on average of 18% of total fatty acids in B. arvensis seeds and was not significantly affected by PGPR inoculation.

Following field trials, shoot height and root weight were both significantly increased (in 8 week samples) by inoculation with LBUM570 in the field (P=0.004 and P=0.04, respectively; Table 3). The shoot height was increased by 10% as compared to the control, while the root weight was increased by 43%. No other treatment caused significant increase in these parameters and the shoot weight was not affected by the different PGPR inoculations. Unlike the growth chamber screenings, the bacterial inoculations had no effect on the seed yield (expressed by g seed/plant) (Table 4).

All parameters relative to total lipid yield and SDA yield were only examined in 8 week samples as the seeds on the plants at 4 weeks were not fully mature. No significant increases were observed for the plant lipid yield when inoculated with the bacterial inoculations as compared to the control, while the only significant increase in SDA yield (by 33% as compared to control) was observed when plants were inoculated with LBUM677 (P=0.05; Table 3).

Figure 2:
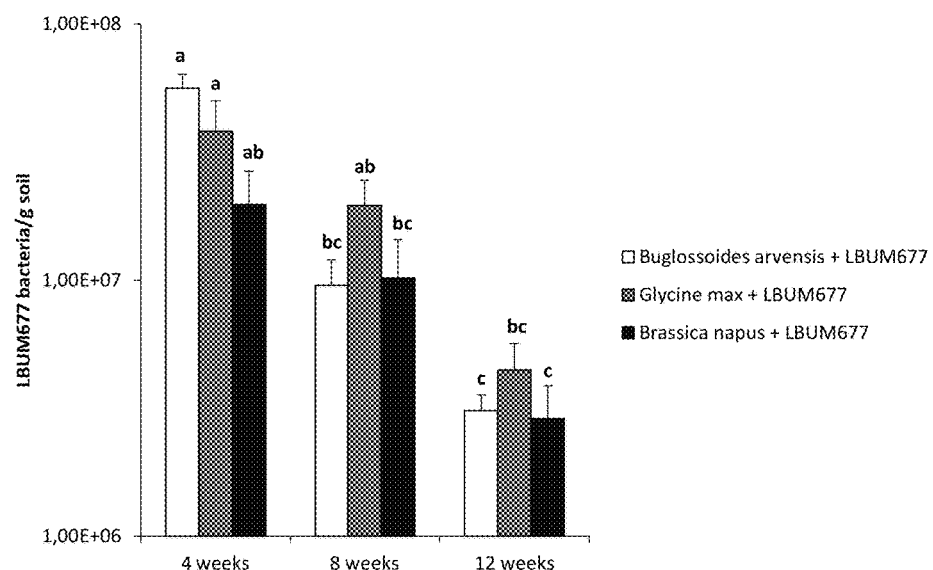
FIG. 2 illustrates the quantity of *P. fluorescens* LBUM677 detected per gram of rhizosphere soil at three different sampling dates.

The results of the additional characterizations of the five most promising PGPRs indicated that LBUM288 belonged to the *Bacillus amyloliquefaciens* species, LBUM361 to the *Stenotrophomonas rhizophila* species, LBUM395 to the *Pseudomonas putida* species, and LBUM570 and LBUM677 belonged to the *Pseudomonas fluorescens* species. Based on the field trial results, we have identified one strain of *Pseudomonas fluorescens* (strain LBUM677) that was able to enhance lipid and SDA yields in B. arvensis in the field and which could be developed for use in a commercial context.

qPCR allowed the detection of a 62 bp DNA fragment specific to LBUM677 from the rhizosphere soil of the three plant species. Absolute quantification of LBUM677 was therefore expressed as amplicon copy number detected per gram of rhizosphere soil. LBUM677 establishment in the rhizosphere was not significantly different between the three plants species. However, a significant (P<0.05) population decline was observed over time (FIG. 2). No interaction between the plant and the time factor was detected. No amplicon was detected in the control samples non-inoculated with LBUM677.

Figure 3:
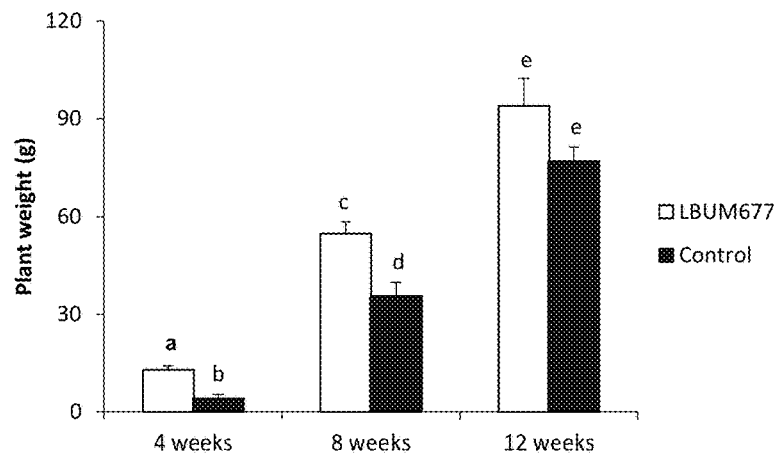
FIG. 3 illustrates the response of *B. napus*' total plant weight to *P. fluorescens* LBUM677 inoculation.
Figure 4:
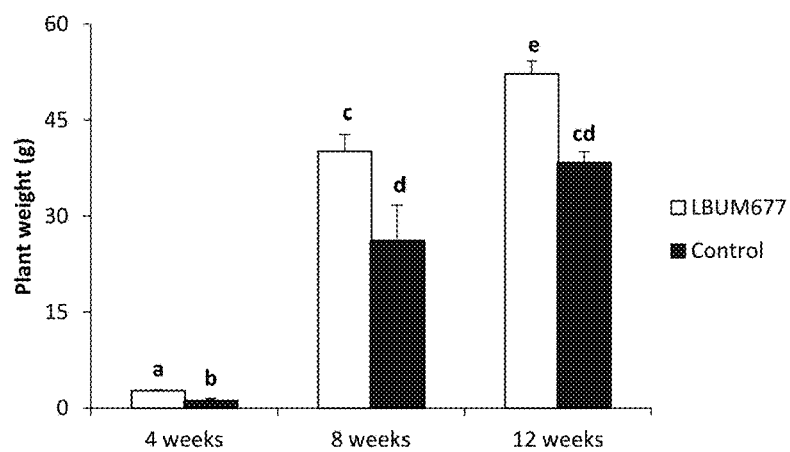
FIG. 4 illustrates the response of *B. arvensis*' total plant weight to *P. fluorescens* LBUM677 inoculation.
Figure 5:
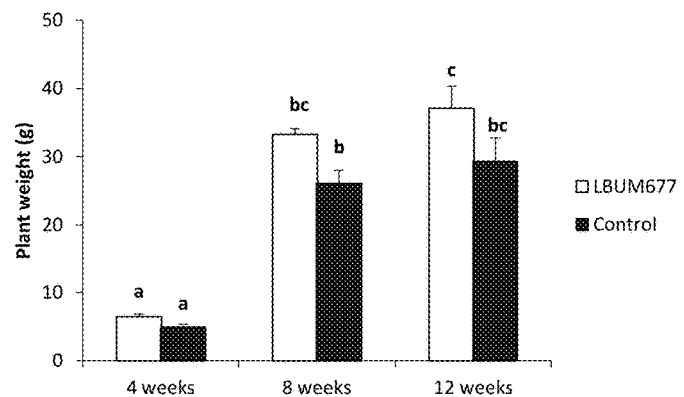
FIG. 5 illustrates the response of *G. max*'s total plant weight to *P. fluorescens* LBUM677 inoculation.

Plant growth promotion since a significant (P<0.05) total plant weight increase was observed in B. napus and B. arvensis when inoculated with LBUM677 compared with the controls. Tukey's posteriori tests also revealed that this significant (P<0.05) increase was observed at all time points (4, 8 and 12 weeks) for both plant species, except at 12 weeks for B. napus. Overall, the plant growth promotion observed led to 53-209% and 26-132% plant weight increase for the different time points for B. napus and B. arvensis respectively (FIGS. 3 and 4). No significant plant growth promotion was observed for G. max when inoculated with LBUM677 (FIG. 5).

Figure 6:
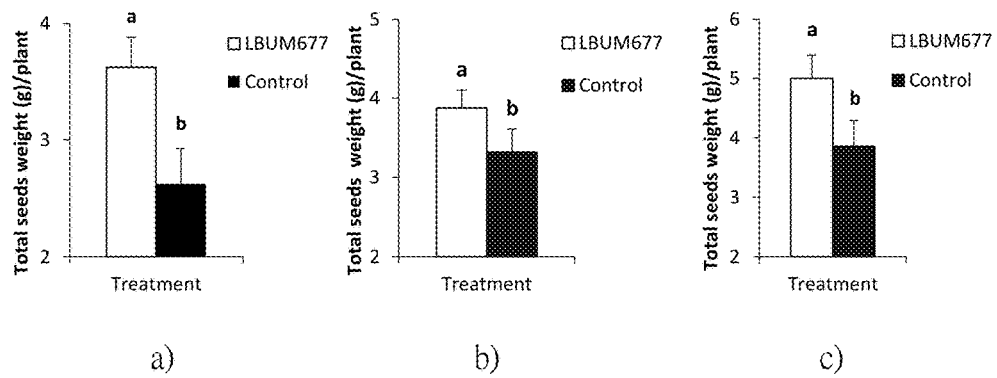
FIG. 6 illustrates the responses of a) *B. napus*', b) *B. arvensis*' and c) *G. max*' total seed weight to *P. fluorescens* LBUM677 inoculation.
Figure 7:
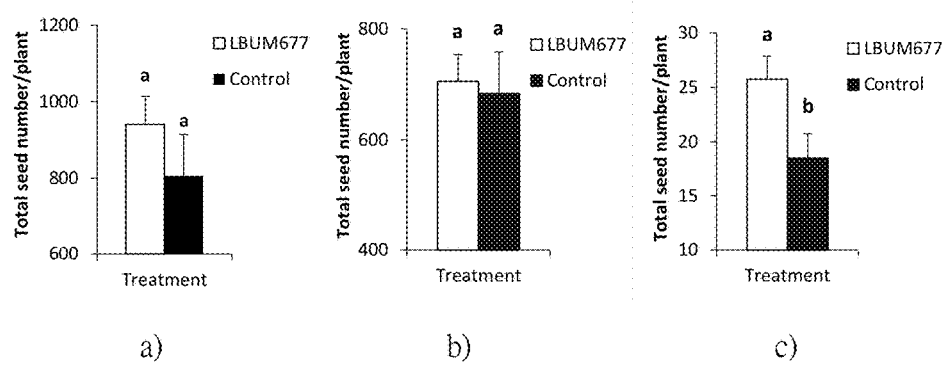
FIG. 7 illustrates the responses of a) *B. napus*', b) *B. arvensis*' and c) *G. max*' seed numbers to *P. fluorescens* LBUM677 inoculation.

Regarding seed production, the inoculation with LBUM677 had a significant (P<0.05) effect on total seed weight produced by all three plant species (FIG. 6). This increase was on average 38%, 16% and 29% for B. napus (FIG. 6a), B. arvensis (FIG. 6b) and G. max (FIG. 6c), respectively. However, no significant increase in total seed numbers produced per plant was observed for B. napus (FIG. 7a) and B. arvensis (FIG. 7b). Only G. max produced significantly (P<0.05) more seeds (39%) when inoculated with LBUM677 (FIG. 7c).

Figure 8:
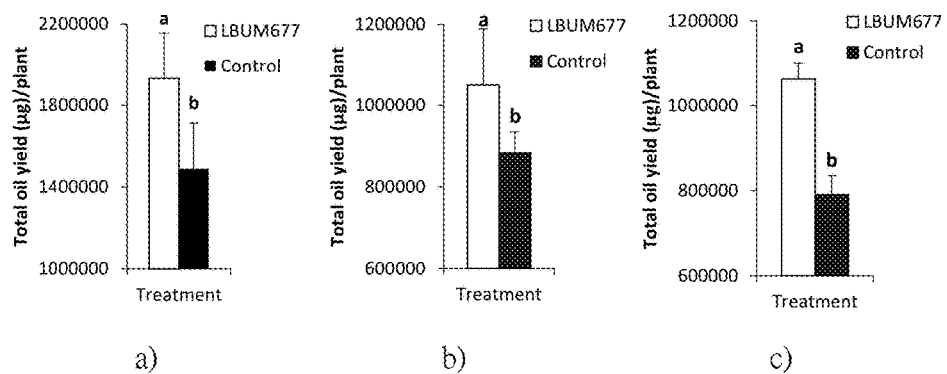
FIG. 8 illustrates the response of a) *B. napus*', b) *B. arvensis*' and c) *G. max*' total oil yield per plant to *P. fluorescens* LBUM677 inoculation.

The inoculation with LBUM677 had a significant (P<0.05) effect on oil yield produced by all three plant species (FIG. 6). This increase was on average 29%, 18% and 34% for B. napus (FIG. 8a), B. arvensis (FIG. 8b) and G. max (FIG. 8c) respectively. FAME analyses also revealed a significant (P<0.05) increase in all the main fatty acids (representing more than 10% of total fatty acids detected per seeds) for the three plant species when inoculated with LBUM677 (Table 4).

*P. fluorescens* LBUM677 colonization resulted in a significant increase in oil yield for all three plant species but to a general plant growth promotion in only two out of three species, B. napus and B. arvensis. Our results showed a clear increase in total seed weight and seed numbers when G. max was inoculated with LBUM677, even though no significant increment in total plant growth was achieved. This shows that plant growth and seed biomass yield are related each other in B. arvenis and B. napus but not necessarily in G. max. However, an oil yield increase was observed when B. napus, B. arvensis and G. max were inoculated with LBUM677 compared with the control plants and this increase was closely correlated with an increase in total seed weight per plant. This could in part be explained by an increased seed number being produced per plant in G. max, but not in B. arvensis and B. napus where no significant seed number increase was detected. Also, a significant impact on the amount of all the major fatty acids such as palmitic (16:00), oleic (18:1n), linoleic (18:2n-6), α-linolenic (18:3n-3) and stearidonic acid (18:4n-3) produced by the plants was achieved in plants inoculated with LBUM677 compared with the controls.

There are very few reports in the literature about improvement in oil seed or fatty acid yields in response to *Pseudomonas* spp. inoculation. However, the present invention described an effect of a *P. fluorescens* strain (LBUM677) on the fatty acid profiles of plant's seeds. Our results showed an increase of 29% in B. napus' oil yield when plants where inoculated with LBUM677, as well as an increase in oil yield of 18% in B. arvensis and 34% in G. max. All the main fatty acids produced by B. napus, B. arvensis and G. max were increased similarly between the different plant species, suggesting that the effect of LBUM677 on fatty acid accumulation is more general than specific and related to a general oil seed yield increase.

*P. fluorescence* LBUM677 is able to colonize the rhizosphere of B. napus, B. arvensis and G. max to similar levels and consequently increase B. arvensis and B. napus' plant weight and total seed weight, as well as oil yield and fatty acids content in all three plant species. This suggests that *P. fluorescens* LBUM677 is a generalist PGPR of oilseed crops and that despite some species-specific differences observed in its effect on different crops, it shown great potential to be used as an inoculum to promote oil yield and fatty acids accumulation in oilseed crops.

Example 1

Screening of the Rhizobacterial Strains

Forty bacterial isolates were selected from a bacterial collection available at the Biotechnology Laboratory at the Université de Moncton (Moncton, Canada; Table 1). The bacteria were selected based on their plant growth promoting potential or because they belong to genera known to contain PGPR. Pure cultures of the selected rhizobacteria were grown at 25° C. and 200 rpm for 48 h in 100 ml Tryptic Soy Broth (Bacto Laboratories Ltd., Burlington, Canada). Concentrations were adjusted to $2 \times 10^8$ CFU/mL based on OD600 nm measurements.

Seeds of *B. arvensis* were provided by Nature's Crops International (Kensington, Canada). Seed germination was performed in a G30 model seed germinator (Conviron, Winnipeg, Canada) using Jiffy-7® peat pellets (Jiffy Products, Shippagan, Canada) under the following conditions: 10° C., 80% relative humidity and 12 h photoperiod. After 21 days, the seedlings were transferred to growth chambers where they were acclimatized for 2 days (identical growth conditions).

The seedlings were inoculated with a given rhizobacterial strain suspended in Tryptic Soy Broth (TSB; (Bacto Laboratories Ltd.) by dipping the plant roots in the prepared rhizobacterial inoculum ($1 \times 10^8$ bacteria/ml) and then transferred in 4-inch diameter pots filled with non-sterilized field soil collected in Bouctouche, Canada. The soil was characterized as a gleyed podzolic gray luvisol, a subgroup of the Canadian System of Soil Classification, with a pH of 5.2, 62% sand, 25% silt, 13% clay, and 2.6% organic matter. Each pot was then inoculated by pipetting an additional 10 ml of the rhizobacterial inoculum directly on the soil surface near the base of the stem. Control treatments were inoculated with sterile TSB.

For the initial growth chamber experiment, the plants were grown following rhizobacterial inoculations in a model PGR15 growth chamber (Conviron) using the following conditions: 20° C., 80% relative humidity and 12 h photoperiod. A total of six replicates for each treatment were used. Due to the limited space in the growth chambers, different treatments were placed in five separate growth chambers (for each treatment, the 6 replicates were always placed in the same growth chamber), with each chamber also containing 6 replicates of control treatments. The plants were watered when needed and 25 mL of Hoagland's mineral solution was added weekly.

Seeds were harvested and counted at 12 weeks following rhizobacterial inoculation, coinciding with plant maturity. One hundred mature seeds were randomly picked and weighted after being dried at 45° C. for one week. Total seed lipid extraction and analysis was performed using duplicate samples of 20 seeds.

Total lipid extraction using hexane as a solvent was optimized for the seeds of *B. arvensis*. Briefly, seeds were mechanically crushed in a 2 mL tube with two 3 mm tungsten carbide beads (Qiagen Inc., Germantown, USA) using the TissueLyser II (Qiagen) at 30 Hz for 6 min. 100 µl of internal standard (Triheptadecanoin; Nu-Chek Prep, Elysian, Minn., USA) was added to each sample before they were transferred to a new glass tube. Hexane was then added and the samples were heated for 10 min at 60° C. and cooled for 2 min before adding 1.5 mL Milli-Q water and centrifuged at 2000 rpm for 5 min to separate phases. The hexane phase was transferred to a new glass tube and the hexane was evaporated from the samples using an N-Evap 112 nitrogen evaporator (Organomation Associates Inc., Berlin, USA). Finally, the tube was weighed to determine the mass of extracted oil. One ml of hexane was then added to the extracted oil and the samples were stored at −20° C. until lipid analysis. Analysis of the fatty acid content was determined by gas chromatography (GC) with flame ionization detection as described in Surette, M. E., et al., *Clinical Therapeutics*, 2003. 25(3): p. 948-971. The following parameters were recorded: oil mass, SDA mass and SDA fatty acid percentage. Total seed yield, lipid yield and SDA yield were calculated based on the total number of seeds to estimate total productivity per plant.

Example 2

Selection of the Rhizobacterial Strains

The five rhizobacterial isolates that showed the most promising results in terms of total seed yield, lipid yield and SDA yield were selected and used for a second growth chamber screening experiment. This experiment was carried out as previously described with the addition of a destructive time-course study to evaluate the effect of the bacterial inoculum on the *B. arvensis* shoot fresh biomass and height at different growth stages. The replicates for each treatment were randomized in a complete block design. Six plants of each treatment were harvested at 4, 8 and 12 weeks following inoculation by cutting the shoot at the base, which was then weighed and measured (destructive sampling). The mature seeds were harvested from the plants at 12 weeks, analyzed as previously mentioned and the experiment was duplicated.

The five rhizobacterial isolates used in the second growth chamber experiment were also used in a field trial screening experiment. The site consisted of an experimental plot used in the cultivation of *B. arvensis* located at Technology Crops International in Hunter River, PEI Canada. The soil was characterized as Alberry Sandy Loam with an organic matter content of 2.1, pH of 6.1, 59% sand, 26% silt and 15% clay.

The experimental plot consisted of a replicated block design where all six treatments were replicated 5 times and each block contained all treatments. The size of the plots was 1.3 m×1.3 m and was measured to contain 100 *B. arvensis* plants per plot. The plants were inoculated by adding 1 L of rhizobacterial inoculum ($1 \times 10^8$ bacteria/ml) to each plot (water was used for control plots) by pouring the inoculum at the base of the plants.

The plants were sampled twice during the growth season at 4 and 8 weeks following rhizobacterial inoculation. The plants sampled at 8 weeks had reached maturity. On each sampling date, 5 plants were uprooted from each plot. Each plant was shaken and the soil still adhering to the roots (rhizosphere soil) was collected and kept on ice. The plant roots were rinsed with water; the plant was measured from the plant collar to the tip and also stored on ice. All samples were then stored at −20° C. until use. The weight of the shoot of each plant (for each sampling date) was measured in the laboratory. The total number of seeds from each plant harvested at 8 weeks was counted and 100 mature seeds were collected from each plant, dried at 45° C. for one week and weighed. Of these 100 seeds, two replicates of 20 seeds were weighed and used for lipid analysis.

Example 3

Identification of the Selected Rhizobacterial Strains

Taxonomical identification of the five most promising rhizobacterial strains was performed by various PCR-based amplifications and sequencing were performed to complement previous 16 rDNA identification of the most promising isolates. The taxonomic markers gyrB and rpoB were amplified respectively using the PCR primers UP-1 and UP-2r and LAPS and LAPS27. PCR-based amplification targeting the ggpS gene (primers ggpSG3i and ggpSG5i) and smeD gene (primers smeD3 and smeD5) of *Stenotrophomonas* spp. was performed on isolate LBUM361. The presence of ggpS and the absence of smeD is characteristic of plant-associated Strenotrophomonas *rhizophila* and not the potential human pathogen *S. malophilia*. All PCR were performed in 50 µl reactions and consisted of 5 µl of a 10×PCR buffer (New England Biolabs, Mississauga, Canada), 5 µl of 5 µM of each primer (Integrated DNA Technologies Inc., Coralville, USA), 1 µl of 10 mM dNTP (New England Biolabs), 1.25 U of Taq DNA polymerase (New England Biolabs), 2 µl of genomic DNA and sterile milli-Q water. The cycling protocol consisted of an initial denaturation of 5 min at 95° C. followed by 40 cycles of denaturation at 95° C. for 40 s, annealing at 60° C. for gyrB, 50° C. for rpoB, 55° C. for ggpS and 58° C. for smeD for 40 s, extension at 72° C. for 2 min and a final extension at 72° C. for 10 min. A gelatinase production test was also performed to distinguish between *P. putida* and *P. fluorescens* strains by stabbing *Pseudomonas* cultures into gelatin media.

Example 4

Characterization of the *P. fluorescens* LBUM677 Strain and its Effect on Oilseed Crops

*P. fluorescens* LBUM677 was originally isolated from the rhizosphere of strawberry plants cultivated in Bouctouche, NB, Canada. LBUM677 was grown in Tryptic Soy Broth (TSB; Bacto Laboratories Ltd., Burlington, Canada), incubated at 25° C. with agitation at 200 rpm for 48 h and concentration was adjusted to $1 \times 10^9$ cells/mL based on OD600 nm measurements. Seeds of *G. max* and *B. napus* were obtained from Pioneer Hi-Bred (Mississauga, ON, Canada) whereas seeds of *B. arvensis* were supplied by Technology Crops International (Kensington, PE, Canada).

The growth chamber experimental set-up consisted of three plant species (*G. max, B. napus* and *B. arvensis*), inoculated or not (control) with LBUM677, four sampling dates (4 weeks, 8 weeks, 12 weeks and at seed maturity) and four replicates per treatment per time. A complete randomize block design was used for a total of 96 experimental units. The whole experiment was repeated a second time. The experiments were conducted in a PGR15 growth chamber (Conviron, Winnipeg, MB, Canada) under the following conditions: 20° C., 80% RH and a photoperiod of 16 h at 500 µmol/m²/s. The soil used was obtained from the research farm Senator Hervé J. Michaud of Agriculture and Agri-Food Canada (Bouctouche, NB, Canada) and characterized as a Gleyed Podzolic Gray Luvisol (GLPZ.GL), according to the Canadian Soil Classification System with 62% sand, 25% silt, 13% of clay, 2.6% organic matter and a pH of 5.2. Seeds of *G. max, B. napus* or *B. arvensis* were sown 1 cm deep in 11.5 cm diameter pots containing 400 g of soil. 10 mL of LBUM677 inoculum ($1 \times 10^9$ cells/mL) was added to the seeds at sowing. Control treatments received 10 mL of water. The pots were first watered 24 h after the inoculation to avoid bacterial leaching and then every two days. The first fertilization was carried out 30 days after sowing and then every two weeks using 100 mL of Hoagland solution per pot.

For plant harvest and soil sampling, destructive sampling was carried out at 4, 8 and 12 weeks, as well at seed maturity (14 weeks for *B. arvensis* and *G. max* and 21 weeks for *B. napus*) for each replication of the experiment. At 4, 8 and 12 weeks, plants were weighted and rhizosphere soil was sampled by shaking the plants to remove loosely adhering soil and collecting only the soil remaining on the roots. Rhizosphere soil was immediately frozen in liquid nitrogen to prevent degradation and then lyophilized using a lyophilizer (Thermo Fisher Scientific, Mississauga, ON, Canada). Samples were stored at −80° C. until DNA extraction. At seed maturity (final harvest only), the total number of seeds per plant, as well as the total seed weight per plant were calculated. The seeds were stored at room temperature until oil extraction and fatty acid profile analysis were performed.

Rhizosphere soil DNA extraction and qPCR quantification of *P. fluorescens* LBUM677 by extracting DNA from 0.25 g of rhizosphere soil samples as described in Griffiths, R. I., et al., *Applied and environmental microbiology*, 2000. 66(12): p. 5488-5491. DNA quantity and quality were evaluated using a NanoDrop ND-1000 spectrophotometer (NanoDrop Technologies, Wilmington, Del., USA). A previously developed PCR primer pair and a TaqMan probe targeting a specific molecular marker (62 bp) in *P. fluorescens* LBUM677 was used to specifically detect and quantify rhizosphere soil populations of LBUM677. qPCR reactions were performed in triplicate on a CFX Connect Real-Time PCR Thermocycler (BioRad, Mississauga, ON, Canada) using the iTaq Universal Probe Supermix kit and protocol (BioRad). Each qPCR reaction mix contained: 10 µL of iTaq Mix, 0.8 µL of 5 µM forward and reverse primer, 0.8 µL of 5 µM TaqMan probe, 4.6 µL of sterile ddH$_2$O and 3 µL of template DNA (diluted 1:10 following extraction) or 3 µL of sterile ddH$_2$O (non-template controls). The cycling protocol consisted of the following steps: 3 min initial denaturation at 95° C., followed by 45 cycles of 10 s at 95° C. and 30 s at 60° C. Each qPCR plate included a standard curve, with values ranging from $5 \times 10^3$ to $5 \times 10^8$ copies. Briefly, the standard curve was prepared by cloning the 62 bp PCR fragment into the pKRX plasmid. The gene copy number was calculated according to the molar mass of the plasmid and amplicon length and the plasmid quantity was measured by spectrophotometry (NanoDrop Technologies).

Seed oil was extracted from seed samples using hexanes as the extraction solvent. Seed were homogenized in 2 mL microcentrifuge tubes using tungsten carbide beads in a Tissue Lyser II (Qiagen, Mississauga, ON, Canada) at 30 Hz for 4 min. Homogenized samples were centrifuged at 14000 g for 1 minute followed by addition of 1 mL of hexanes and 100 µL of triheptadecanoin/chloroform solution (internal standard; Nu-Chek Prep, Elysian, Minn., USA). 2 mL of saturated NaCl solution was added and the tubes were centrifuged for 5 min at 1300 g to separate the solution in two phases. The upper organic phase was transferred into pre-weighed 13×100 mm glass tubes to isolate the oil by evaporating the hexanes under a stream of nitrogen (N-Evap 112 OA-SYS) until the samples were clear and mass was stable (on average 15 min). Isolated samples were weighed to obtain extracted oil mass and then suspended in hexanes to isolate the fatty acid methyl esters (FAMEs) by hydrolyzing the oil samples with 400 µL of 0.5 M KOH/MeOH for 15 min at 100° C. followed by transmethylation in 1 mL of 14% BF$_3$-MeOH for 10 min at 100° C. The resulting solution was partitioned between 2 mL of hexanes and 2 mL of saturated NaCl solution, vortexed, and the upper organic phase containing FAMEs was collected for analysis by gas chromatography. FAMEs were separated and quantified on a Trace Gas Chromatograph Ultra (Thermo Finnigan, Mississauga, ON, Canada) equipped with a FID detector and a BPX70 column (30 m×0.25 mm internal diameter (i.d.), 0.25 μm film thickness) (SGE Analytical Science, Victoria, Australia). The carrier gas was He, which was supplied at a flow rate of 1 mL/min. The oven temperature was ramped from 150 to 180° C. at a rate of 10° C./min, followed by an increase to 205° C. at 1.5° C./min, and finally by an increase to 255° C. at a rate of 35° C./min and was held for 1.9 min. The temperatures of the injector and detector were 250° C. FAMEs peak identities and quantities were determined by retention times and standard curves of known standards using Triheptadecanoin (Nu-Chek Prep, Elysian, Minn., USA) as an internal standard.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for enhancing total lipid yields in an oilseed crop, comprising a step of inoculating the oilseed crop chosen from soy (*Glycine max*) and canola (*Brassica napus*) with a *Pseudomonas fluorescens* strain deposited under ATCC Patent Deposit Designation No. PTA-123874 filed on Mar. 9, 2017 at a quantity of at least $1 \times 10^7$ to $1 \times 10^9$ bacterial cells/plant, the *Pseudomonas fluorescens* strain having a nucleic acid molecule comprising a nucleotide sequence consisting of:

```
                                          (SEQ ID NO.: 5)
5'CTACGGCAAGGCGACGCTGACGTGTGCAAAGGTTGTACCCGTTTCAC

CACATCAGCCGGCTGCGCCTGCATCGCGGTCTTGATCATAGACTCGGAA

TTGTCCGCGCCAATGATCACCCGATTGGGTTTTTCCGCCAGCAACGGCC

AGAAACGCCCTGCACCACACGGCAGATCCAGAACCAGCCCCGGCTCGCC

CGTCAGCGTCGCCTTGCCGTAG3',
``` wherein the *Pseudomonas fluorescens* strain is in association with a biologically acceptable carrier; and wherein the *Pseudomonas fluorescens* strain increases total lipid yields in the oilseed crop relative to oilseed crop not exposed to the *Pseudomonas fluorescens* strain.

2. The method of claim 1, wherein the *Pseudomonas fluorescens* strain increases growth yields of the oilseed crop by at least 15% to 215% relative to oilseed crop not exposed to the *Pseudomonas fluorescens* strain.

3. The method of claim 1, wherein *Pseudomonas fluorescens* strain increases seed yields of the oilseed crop by at least 10% to 45% relative to oilseed crop not exposed to the *Pseudomonas fluorescens* strain.

4. The method of claim 1, wherein the *Pseudomonas fluorescens* strain increases total lipid yields of the oilseed crop by at least 10% to 45% relative to oilseed crop not exposed to the *Pseudomonas fluorescens* strain.

* * * * *